United States Patent [19]

Nakamura et al.

[11] 4,115,398
[45] Sep. 19, 1978

[54] ISOINDOLINE DERIVATIVES AND THE ACID ADDITION SALTS THEREOF AND PROCESS FOR THE PREPARATION OF SAME

[75] Inventors: Koji Nakamura, Kodaira; Haruo Otaki, Fuji; Yutaka Yamamoto, Higashimurayama; Noboru Shimizu, Higashimurayama; Kiyoshi Kawamura, Higashimurayama; Seiichi Sato, Higashimurayama, all of Japan

[73] Assignee: Kowa Company Ltd., Nagoya, Japan

[21] Appl. No.: 757,028

[22] Filed: Jan. 5, 1977

[51] Int. Cl.² .......................................... C07D 209/44
[52] U.S. Cl. .................................................. 260/326.1
[58] Field of Search .................................... 260/326.1

[56] References Cited
PUBLICATIONS

Chem. Abstracts 83: P206482f.

*Primary Examiner*—Ethel G. Love
*Attorney, Agent, or Firm*—Sherman & Shalloway

[57] ABSTRACT

Isoindoline derivatives of the formula

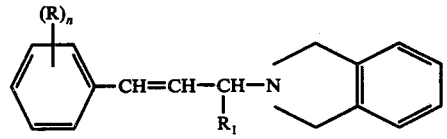

(I)

and the pharmaceutically acceptable acid addition salts thereof, wherein R represents a moiety selected from the group consisting of hydrogen, halogen, lower alkyl, lower alkoxy, nitro, hydroxy and hydroxy lower alkyl, and $n$ is a positive number from 1 to 3, which R's may be the same or different when $n$ is 2 or 3, and when $n$ is 2, the two R's may be joined to the carbon atom vicinal to the phenyl ring to which the two R's are joined and may taken together form lower alkylenedioxy and the group

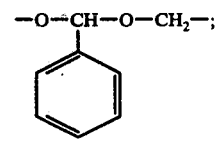

and $R_1$ is a member of the group consisting of hydrogen and lower alkyl.

The compounds of this invention can be readily prepared by reacting a compound of the formula

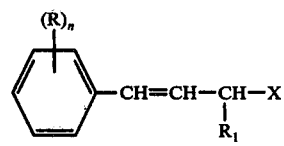

wherein R represents, in addition to the above defined, alkoxycarbonyloxy; $R_1$ and $n$ are as defined above; and X is halogen or the groups $-O-SO_2-Y$ where Y is either lower alkyl or aryl, with isoindoline of the formula

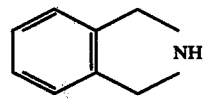

or a minemal acid salt thereof. The compounds are useful in such fields as, for example cardiovascular drugs.

8 Claims, No Drawings

ISOINDOLINE DERIVATIVES AND THE ACID ADDITION SALTS THEREOF AND PROCESS FOR THE PREPARATION OF SAME

This invention relates to new isoindoline derivatives and their pharmaceutically acceptable acid addition salts and a process for their preparation.

More specifically, this invention relates to isoindoline derivatives of the formula

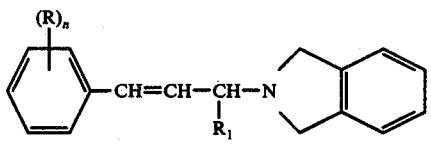
(I)

and the pharmaceutically acceptable acid addition salt thereof and a process for preparing the foregoing isoindoline derivatives and their acid addition salts, in which formula (I) R represents a moiety selected from the group consisting of hydrogen, halogen, lower alkyl, lower alkoxy, nitro, hydroxy and hydroxy lower alkyl, and $n$ is a positive number from 1 to 3, which R's may be the same or different when $n$ is 2 or 3, and when $n$ is 2, the two R's may be joined to the carbon atom vicinal to the phenyl ring to which the two R's are joined and may taken together form lower alkylenedioxy and the group

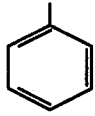
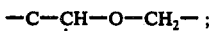

and $R_1$ is a member of the group consisting of hydrogen and lower alkyl.

The isoindoline derivatives of the foregoing formula (I) and their pharmaceutically acceptable acid addition salts are new compounds which, demonstrating such biochemical actions as, for example, vasodilating action, anti-serotonergic action and alpha-andrenergic blocking action, are valuable for use in such fields as, for example cardiovascular drugs.

It is therefore an object of the present invention to provide these useful new compounds of formula (I) and their pharmaceutically acceptable acid addition salts.

Another object of the present invention is to provide a process for preparing the foregoing compounds.

Other objects and advantages of the present invention will become apparent from the following description.

The foregoing compounds of formula (I) of the present invention can be readily prepared in good yield, say, by reacting a compound of the formula

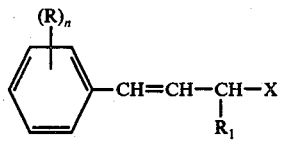
(II)

wherein R, in addition to being as above defined, may also be either acyloxy

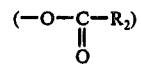

or alkoxycarbonyloxy

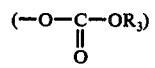

where $R_2$ and $R_3$ are lower alkyl, preferably $C_1$-$C_4$ alkyl, or aryl, preferably phenyl, or aralkyl, preferably benzyl; $R_1$ and $n$ are as defined above; and X is either halogen or the group —O—SO$_2$—Y where Y is either lower alkyl, preferably $C_1$-$C_4$ alkyl, and more preferably $C_1$-$C_3$ alkyl, or aryl, preferably phenyl or naphthyl which may contain a $C_1$-$C_2$ alkyl radical or halogen; with isoindoline of the formula

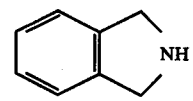
(III)

or a mineral acid salt thereof followed by alkylation or hydrolysis of the resulting product.

The foregoing compound of formula (II) that is used as the starting material in this invention can be readily obtained either by reacting a compound of the formula

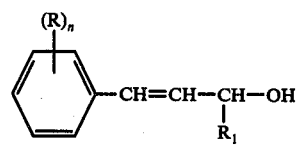
(IV)

wherein R is the aforementiond groups or acyloxy or alkoxycarbonyloxy, and $R_1$ and $n$ are as above defined, with a halogenating agent to halogenate the compound of formula (IV) to convert it to a compound in which X in the formula (II) is halogen, or by reacting said compound of formula (IV) with a halide of a sulfonic acid to transform the compound of formula (IV) to a sulfonic acid ester, a compound in which X in the formula (II) is the group —O—SO$_2$—Y where Y is as above defined.

Examples of the halogenating agents include such compounds as hydrochloric acid, thionyl chloride, phosphorus trichloride, phosphorus pentachloride, phosphorus oxychloride, hydrobromic acid, thionyl bromide, phosphorus tribromide, phosphorus pentabromide, phosphorus oxybromide and hydriodic acid. The halogenation reaction using these halogenating agents can be carried out, for example, in the following manner. The reaction is carried out in the presence or absence of a solvent for 1-6 hours at room temperature to 70° C. (about the refluxing temperature of the solvent), using 1-2 equimolar quantities of thionyl chloride. After completion of the reaction, ice water is added, and the reaction product is washed with water. This is followed by extraction of the reaction product with a solvent. The product is then dried and the solvent is distilled off to obtain an oily product. On distillation of this product under reduced pressure, a colorless oily product (II) is obtained. Usable as the solvent are ether, benzene, methylene chloride and chloroform.

On the other hand, as the foregoing halides of sulfonic acid, there can be mentioned such compounds as, for example, methanesulfonyl chloride, ethanesulfonyl chloride, benzenesulfonyl chloride, p-toluenesulfonyl chloride, p-bromobenzenesulfonyl chloride, and alpha- and beta-naphthalenesulfonyl chloride. The sulfonic acid esterification reaction, such as described hereinabove, can be carried out, say, by reacting the compound of formula (IV) with an equimolar or somewhat excess of the halide of sulfonic acid in a solvent at a temperature ranging from −20° C. to the boiling point of the solvent. As the solvent to be used in this case, usable are pyridine and such other solvents as benzene, toluene, ether, chloroform, dichloromethane and hexane, as well as the solvent mixtures of these latter solvents and pyridine or triethylamine.

Further, the isoindoline of the foregoing formula (III) can be readily prepared from phthalimide, say, in accordance with the process described in the *Journal of Pharmaceutical Science,* vol. 53, p. 981, 1964. On the other hand, the mineral acid salts thereof can be prepared, say, by dissolving isoindoline in a hydrochloric acid-methanol solution and thereafter distilling off the methanol.

The foregoing compounds of formulas (II) and (III) obtained as above described are reacted in the process of this invention. In this case, when as the compound of formula (II) that in which X is a halogen atom is used, the reaction can be carried out at room temperature in the presence of a solvent and, if desired, in the presence of an alkali. Since the reaction proceeds at room temperature, heating or cooling of the reaction mixture is not especially required, and a temperature of about 20° to about 100° C. can be employed. The reaction can be completed, say, in about 1–15 hours. The solvent to be used in this case are such lower alcohols as methanol or ethanol, such aromatic hydrocarbons as benzene or toluene, such halogenated hydrocarbons as chloroform or methylene chloride, and such ethers as diethyl ether or dioxane. Examples of the alkalis include the alkali metal hydroxides such as sodium hydroxide or potassium hydroxide, the alkali carbonates such as sodium carbonate or potassium carbonate, the alkyl amines such as triethylamine, and the cyclic amines such as pyridine.

When a compound in which X is —O—SO$_2$—Y is used as the compound of formula (II) in carrying out the reaction between the compound of formula (II) and the compound of formula (III), there is no need to use a solvent, and the compounds of formula (II) and formula (III) need only be brought into contact with each other. While the reaction proceeds even at room temperature, the application of heat is preferred. For instance, a temperature of from about 10° to about 200° C. is frequently employed. The reaction can be completed, say, in about one hour to about 15 hours.

When as the compound of formula (II) that in which R is acyloxy or alkoxycarbonyloxy is used in the process of this invention, the deacylation or dealkoxycarbonylation reaction proceeds concurrently and, as a result, it becomes possible to form as the commpound of formula (I) that in which R is hydroxy. According to the invention process the compound of formula (I) in which R is hydroxy can be transformed to a compound of formula (I) in which R is alkoxy, say, by reacting the former with a diazoalkyl compound such as diazomethane and diazoethane or an alkylating agent, e.g., a sulfuric acid alkyl ester, such as dimethyl sulfate or diethyl sulfate, methyl fluorosulfate, methyl iodide, methyl bromide and ethyl iodide. On the other hand, the compound of formula (I) in which n being 2 the two R's taken together form either lower alkylenedioxy or the group

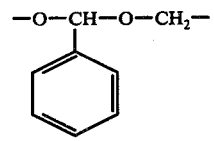

can be transformed into a compound of formula (I) in which R is either hydroxy or hydroxy lower alkyl, say, by hydrolyzing the former by heating it for 1–5 hours at 0°–100° C. under acidic conditions using such acids as hydrochloric acid, sulfuric acid, hydrobromic acid, oxalic acid and acetic acid. Further, the compound of formula (I), which can thus be prepared readily and in good yield from the compounds of formulas (II) and (III), can be converted to a suitable acid addition salt, especially a pharmaceutically acceptable acid addition salt. This conversion to an acid addition salt can be utilized as a means of purifying the product. Again, the resulting acid addition salt can be reverted to the compound of formula (I), say, by a procedure consisting of dissolving the salt in water, neutralizing the resulting solution with an alkali and thereafter submitting the solution to solvent extraction to eliminate the acid. Acids that are suitably used for forming the foregoing acid addition salts include, for example, the inorganic acids such as hydrochloric acid, hydrobromic acid, hydroiodic acid, sulfuric acid, phosphoric acid and nitric acid, and the organic acids such as acetic acid, propionic acid, methanesulfonic acid, benzenesulfonic acid, oxalic acid, succinic acid, maleic acid, fumaric acid, citric acid, lactic acid, malic acid and tartaric acid.

In the new isoindoline derivatives of formula (I) of the present invention, as R in the formula (I) the preferred halogens are chlorine, bromine and fluorine. On the other hand, the lower alkyl radicals preferred as R are the straight chain or branched $C_1$–$C_4$ alkyl radicals, and more preferably the straight chain or branched $C_1$–$C_3$ alkyl radicals. As examples of these alkyl radicals, mention can be made of such radicals as methyl, ethyl, n- or iso-propyl and n-, iso-, sec- or tert-butyl. Further, the lower alkoxy radicals preferred as R are the straight chain or branched $C_1$–$C_4$ alkoxy radicals, more preferably the $C_1$–$C_3$ alkoxy radicals and especially the $C_1$–$C_2$ alkoxy radicals, As these alkoxy radicals, those corresponding to the alkyl radicals illustrated hereinabove can be mentioned. On the other hand, the hydroxy lower alkyl radicals preferred as R include the hydroxy $C_1$–$C_4$ alkyl radicals, and more preferably the hydroxy $C_1$–$C_2$ alkyl radicals. Further, the lower alkylenedioxy radicals preferred as R are the $C_1$–$C_2$ alkylenedioxy radicals. As regards $R_1$ of the formula (I) representing the new isoindoline derivatives of the present invention, the lower alkyl radicals that have been indicated as being preferred or especially preferred and the specific examples thereof that have been mentioned in connection with R are equally applicable in the case of $R_1$.

The typical compounds (I) shown in the hereinafter given examples have been summarized in the following Table 1.

Table 1

| No.* | R | n | $R_1$ | m.p. (° C.) | Salt | Properties | Formula |
|---|---|---|---|---|---|---|---|
| 1 | H | 1 | H | 180 – 182 (d.) | HCl | colorless prismatic crystals | $C_{17}H_{18}NCl$ |
| 2 | H | 1 | $CH_3$ | oil (confirmed by NMR) | — | oil | $C_{18}H_{19}N$ |
| 3 | 2-Cl | 1 | H | 170 – 172 (d.) | HCl | colorless acicular crystals | $C_{17}H_{17}NCl_2$ |
| 4 | 3-Cl | 1 | " | 187.5 – 188.5 | oxalic acid | " | $C_{19}H_{18}O_4NCl$ |
| 5 | 4-Cl | 1 | " | 159 – 160 | maleic acid | colorless prismatic crystals | $C_{21}H_{20}O_4NCl$ |
| 6 | 2-Br | 1 | " | 166 – 167 (d.) | " | " | $C_{21}H_{20}O_4NBr$ |
| 7 | 2-F | 1 | " | 149 – 151 | " | " | $C_{21}H_{20}O_4NF$ |
| 8 | 2-Cl, 4-Cl | 2 | " | 146 – 148 (d.) | " | colorless acicular crystals | $C_{21}H_{19}O_4NCl_2$ |
| 9 | 2-Cl, 6-Cl | 2 | " | 156 – 158 | " | colorless prismatic crystals | $C_{21}H_{19}O_4NCl_2$ |
| 10 | 3-Cl, 4-Cl | 2 | " | 133.5 – 135.5 | " | colorless acicular crystals | $C_{21}H_{19}O_4NCl_2$ |
| 11 | 2-$CH_3$ | 1 | " | 140 – 142 | " | colorless prismatic crystals | $C_{22}H_{23}O_4N$ |
| 12 | 3-$CH_3$ | 1 | " | 132 – 134 | " | colorless acicular crystals | $C_{22}H_{23}O_4N$ |
| 13 | 4-$CH_3$ | 1 | " | 213 – 214 (d.) | HCl | " | $C_{18}H_{20}NCl$ |
| 14 | 4-$CH(CH_3)_2$ (isopropyl) | 1 | " | 158 – 160 | maleic acid | colorless prismatic crystals | $C_{24}H_{27}O_4N$ |
| 15 | 2-$OCH_3$ | 1 | " | 147 – 148 | " | colorless acicular crystals | $C_{22}H_{23}O_5N$ |
| 16 | 3-$OCH_3$ | 1 | " | 135 – 136 | " | " | $C_{22}H_{23}O_5N$ |
| 17 | 4-$OCH_3$ | 1 | " | 201 – 202 (d.) | HCl | " | $C_{18}H_{20}ONCl$ |
| 18 | 2-$OC_2H_5$ | 1 | " | 156 – 158 | maleic acid | " | $C_{23}H_{25}O_5N$ |
| 19 | 3-$OCH_3$, 4-$OCH_3$ | 2 | " | 137.5 (d.) | " | " | $C_{23}H_{25}O_6N$ |
| 20 | 3-$OCH_3$, 4-$OCH_3$, 5-$OCH_3$ | 3 | " | 192 – 193 (d.) | oxalic acid | colorless prismatic crystals | $C_{22}H_{25}O_7N$ |
| 21 | 2-$NO_2$ | 1 | " | 144 – 146 | maleic acid | pale yellow prismatic crystals | $C_{21}H_{20}O_6N_2$ |
| 22 | 3-$NO_2$ | 1 | " | 208 – 210 (d.) | HCl | colorless acicular crystals | $C_{17}H_{17}O_2N_2Cl$ |
| 23 | 4-$NO_2$ | 1 | " | 168 – 170 (d.) | maleic acid | pale yellow prismatic crystals | $C_{21}H_{20}O_6N_2$ |
| 24 | 2-OH | 1 | " | 161 – 163 (d.) | — | colorless acicular crystals | $C_{17}H_{17}ON$ |
| 25 | 3-OH | 1 | " | 164.5 – 165.5 | — | " | $C_{17}H_{17}ON$ |
| 26 | 4-OH | 1 | " | 213 – 214 (d.) | HCl | " | $C_{17}H_{18}ONCl$ |
| 27 | 3-OH, 4-OH | 2 | " | 160.5 (d.) | — | light yellow petaloid crystals | $C_{17}H_{17}O_2N$ |
| 28 | 4-OH, 3-$OCH_3$ | 2 | " | 162 – 164 (d.) | maleic acid | colorless leaflike crystals | $C_{23}H_{25}O_5N$ |
| 29 | 4-OH, 3-$CH_2OH$ | 2 | " | 177 – 178 | — | yellow sheetlike crystals | $C_{18}H_{19}O_3N$ |
| 30 | 3,4-O—$CH_2$—O— | 2 | " | 209 – 211 (d.) | HCl | colorless prismatic crystals | $C_{18}H_{18}O_2NCl$ |
| 31 | 3,4-O—CH—O—$CH_2$— 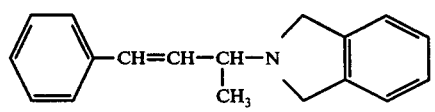 | 2 | " | 201 – 202 | maleic acid | colorless acicular crystals | $C_{29}H_{27}O_6N$ |
| 32 | 3-Br | 1 | " | 131 – 133 | " | " | $C_{21}H_{20}O_4NBr$ |
| 33 | 2-$OCH_3$, 3-$OCH_3$ | 2 | " | 123 – 125 | " | " | $C_{23}H_{25}O_6N$ |

*The numbers correspond to the hereinafter given Example numbers.

The following examples will serve to more fully illustrate the many modes of practicing the present invention.

EXAMPLE 1-a

N-cinnamylisoindoline

The process for preparing this compound and its physical properties will be shown below. A mixture of 1.8 grams of isoindoline, 2.5 grams of cinnamyl chloride, 4 milliliters of triethylamine and 40 milliliters of ethanol is stirred for 4 hours at room temperature. After completion of the reaction, the solvent is distilled off, after which water is added to the residue and extracted with ether. The ether layer is collected and dried followed by distilling the ether off. The so obtained oily product is converted to a hydrochloride in a customary manner and then recrystallized from methyl ethyl ketone to obtain 1.4 grams (yield 34.6%) of N-cinnamylisoindoline hydrochloride as crystals having a melting point of 180°–182° C. (decomposition).

Elementary analysis:

|  | C | H | N |
|---|---|---|---|
| Calcd. (%) for $C_{17}H_{17}N \cdot HCl$: | 75.12 | 6.68 | 5.15 |
| Found (%): | 74.93 | 6.73 | 4.93 |

EXAMPLE 1-b

A mixture of 4.76 grams of isoindoline and 2.74 grams of O-(p-tosyl)-cinnamyl alcohol is heated for 3 hours at a bath temperature of 100° C. with stirring. After completion of the reaction, the reaction mixture is rendered alkaline by the addition of 10% sodium hydroxide and extracted with chloroform. The chloroform layer is collected and purified by silica gel column chromatography, after which the resulting oily product is treated as in Example 1-a to obtain 1.06 grams (yield 39%) of N-cinnamylisoindoline hydrochloride as crystals having a melting point of 180°–182° C. (decomposition). The infrared spectrum of this product was in complete agreement with that of the product obtained in Example 1-a.

EXAMPLE 2

3-Isoindolino-1-phenyl-1-butene

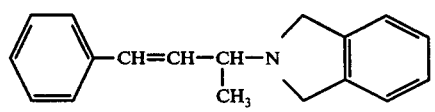

The process for the preparation of this compound and its physical properties will be given below. A solution of 7.5 grams of isoindoline in 20 milliliters is added dropwise to a solution of 5.2 grams of 3-chloro-1-phenyl-1-butene in 30 milliliters of methanol followed by stirring the mixture for 3 hours at room temperature. After completion of the reaction, the solvent is distilled off from the reaction mixture, following which the reaction mixture is extracted with chloroform and purified by silica gel column chromatography to obtain 2.65 grams (yield 34.0%) of 3-isoindolino-1-phenyl-1-butene as an oily product.

NMR value: $\delta_{CCl_4}^{TMS}$ ppm
1.25 (3H, d, J=6cps, branched methyl)
3.23 (4H, s, isoindoline nucleus methyl)
4.0–3.57 (1H, m, allyl position methine)
6.62–5.78 (2H, m, olefin)
7.25 (9H, b, s, aromatic)

EXAMPLE 3

N-(o-chlorocinnamyl)-isoindoline

The process for the preparation of this compound and its physical properties will be given below. A solution of 3.46 grams of o-chlorocinnamyl chloride and 4.41 grams of isoindoline in 20 milliliters of ethanol is stirred for 12 hours at room temperature. After cmmpletion of the reaction, the solvent is distilled off. The resulting residue is then rendered alkaline by the addition of 10% sodium hydroxide and extracted with chloroform. The chloroform layer is then purified by silica gel column chromatography, and the resulting oily product is treated as in Example 1-a to obtain 2.32 grams (yield 41% of N-(o-chlorocinnamyl)-isoindoline hydrochloride as crystals having a melting point of 170°–172° C. (decomposition).

Elementary analysis:

|  | C | H | N |
|---|---|---|---|
| Calcd. (%) for $C_{17}H_{16}ClN \cdot HCl$: | 66.67 | 5.60 | 4.57 |
| Found (%): | 66.81 | 5.55 | 4.67 |

EXAMPLES 4–12

Example 1-a is repeated but using instead of cinnamyl chloride the cinnamyl chlorides having the substituents shown in Nos. 4–12 of the hereinbefore-given Table 1 to obtain the compounds of Nos. 4–12 shown in said Table 1.

EXAMPLE 13

N-(p-methylcinnamyl)-isoindoline

The process for the preparation of this compound and its physical properties will be given below. A solution of 5 grams of p-methylcinnamyl chloride in 50 milliliters of ethanol is added dropwise to a solution of 8.93 grams of isoindoline in 50 milliliters of ethanol, following which the mixture is stirred overnight at room temperature. After completion of the reaction, the reaction mixture is concentrated followed by adding chloroform to the residue and filtering the insolubles off. Next, the solvent is distilled off, and the residue is purified by silica gel column chromatography to obtain an oily product, which is transformed into a hydrochloride in a customary manner and recrystallized from a methanol-ether mixture to obtain 4.1 grams (yield 47.8%) of N-(p-methylcinnamyl)-isoindoline hydrochloride as crystals having a melting point of 213°–214° C. (decomposition).

Elementary analysis:

|  | C | H | N |
|---|---|---|---|
| Calcd. (%) for $C_{18}H_{19}N \cdot HCl$: | 75.64 | 7.05 | 4.90 |
| Found (%): | 75.35 | 7.04 | 4.95 |

EXAMPLE 14

The experiment is carried out as in Example 1-a but using 4-isopropylcinnamyl chloride instead of cinnamyl chloride to obtain the compound of No. 14 shown in the hereinbefore-given Table 1.

EXAMPLE 15

N-(o-methoxycinnamyl)-isoindoline

The process for the preparation of this compound and its physical properties will be given below. 236.2 milligrams of the N-(o-hydroxycinnamyl)-isoindoline of the hereinafter-given Example 24 is dissolved in 10 milliliters of ethanol. After adding an ether solution of diazomethane thereto, the resulting mixture is left standing overnight at room temperature. The excess diazomethane is then decomposed with acetic acid, the solvent is distilled off, and the residue is recrystallized from acetone as a maleic acid salt to obtain 220.2 milligrams (yield 61.2%) of N-(o-methoxycinnamyl)-isoindoline.-maleic acid salt as crystals having a melting point of 147°–148° C.

Elemental analysis:

|  | C | H | N |
|---|---|---|---|
| Calcd. (%) for $C_{18}H_{19}NO \cdot C_4H_4O_4$: | 69.27 | 6.08 | 3.67 |
| Found (%): | 69.06 | 6.05 | 3.64 |

EXAMPLE 16

Example 1-a is repeated but using 3-methoxycinnamyl chloride instead of cinnamyl chloride to obtain the compound of No. 16 shown in the hereinbefore-given Table 1.

EXAMPLE 17

N-(p-methoxycinnamyl)-isoindoline

The process for the preparation of this compound and its physical properties will be given below.

A solution of 0.45 gram of p-methoxycinnamyl chloride and 0.62 gram of isoindoline in 20 milliliters of ethanol is stirred overnight at room temperature. After completion of the reaction, the reaction mixture is concentrated. Chloroform is then added to the residue, and the insolubles are filtered off. The subsequent operations are carried out as in Example 13 to obtain 0.17 gram (yield 37.7%) of N-(p-methoxycinnamyl)-isoindoline hydrochloride as crystals having a melting point of 201°–202° C. (decomposition).

Elementary analysis:

|  | C | H | N |
|---|---|---|---|
| Calcd. (%) for $C_{18}H_{19}NO \cdot HCl$: | 71.63 | 6.68 | 4.64 |
| Found (%) | 71.53 | 6.63 | 4.56 |

EXAMPLE 18

Example 1-a is repeated but using 2-ethoxycinnamyl chloride instead of cinnamyl chloride to obtain the compound of No. 18 shown in the hereinbefore-given Table 1.

EXAMPLE 19

N-(3,4-dimethoxycinnamyl)-isoindoline

The process for the preparation of this compound and its physical properties will be given below. 2.1 grams of the N-(4-hydroxy-3-methoxycinnamyl)-isoindoline of the hereinafter-given Example 28 is dissolved in 40 milliliters of methanol. After adding 120 grams of an ether solution of diazomethane thereto, the resulting mixture is left standing overnight at room temperature. The reaction mixture is then concentrated and dried to obtain 2.4 grams of yellow-brown crystals. These crystals are then converted to a maleic acid salt in a customary manner by reacting 1.0 grams of maleic acid therewith. These crystals are then recrystallized from acetone to obtain 1.7 grams (yield 55.4%) of N-(3,4-dimethoxycinnamyl)-isoindoline.maleic acid salt as colorless acicular crystals having a melting point of 137.5° C. (decomposition).

Elementary analysis:

|  | C | H | N |
|---|---|---|---|
| Calcd. (%) for $C_{19}H_{21}NO_2 \cdot C_4O_4H_4$: | 67.14 | 6.12 | 3.40 |
| Found (%): | 67.12 | 6.11 | 3.39 |

EXAMPLES 20-21

The experiments are carried out as in Example 1-a but using 3,4,5-methoxycinnamyl chloride and 2-nitrocinnamyl chloride instead of cinnamyl chloride to obtain the compounds of Nos. 20 and 21, respectively, shown in the hereinbefore-given Table 1.

EXAMPLE 22

N-(m-nitrocinnamyl)-isoindoline

The process for the preparation of this compound and its physical properties will be given below. A solution of 5.68 grams of isoindoline hydrochloride and 2.86 grams of sodium hydroxide in 15 milliliters of water is added to a solution of 6.8 grams of m-nitrocinnamyl chloride in 160 milliliters of ethanol, and the mixture is stirred for 10 hours at room temperature. After completion of the reaction, the reaction product is concentrated, and the residue is extracted with chloroform. The extract is then purified by silica gel column chromatography, following which the resulting oily product is converted to a hydrochloride in a customary manner and recrystallized from ethanol to obtain 5.6 grams (yield 52%) of N-(m-nitrocinnamyl)-isoindoline hydrochloride as crystals having a melting point of 208°–210° C. (decomposition).

Elementary analysis:

|  | C | H | N |
|---|---|---|---|
| Calcd. (%) for $C_{17}H_{16}N_2O_2O_2 \cdot HCl$: | 64.45 | 5.41 | 8.84 |
| Found (%): | 64.71 | 5.35 | 9.01 |

EXAMPLE 23

Example 1-a is repeated but using 4-nitrocinnamyl chloride instead of cinnamyl chloride to obtain the compound No. 23 shown in the hereinbefore-given Table 1.

EXAMPLE 24

N-(o-hydroxycinnamyl)-isoindoline

The process for the preparation of this compound and its physical properties will be given below. A solution of 5.8 grams of isoindoline in 20 milliliters of methanol is added dropwise to a solution of 3.3 grams of o-ethoxycarbonyloxycinnamyl chloride in 30 milliliters of methanol, and the resulting mixture is stirred for 1 hour at room temperature. After completion of the reaction, the methanol is distilled off, and the residue is extracted with chloroform. The chloroform layer is then purified by silica gel column chromatography and recrystallized from ethanol to obtain 1.2 grams (yield 35%) of N-(o-hydroxycinnamyl)-isoindoline as crystals having a melting point of 161°–163° C. (decomposition).

Elementary analysis:

|  | C | H | N |
|---|---|---|---|
| Calcd. (%) for $C_{17}H_{17}NO$: | 81.24 | 6.82 | 5.57 |
| Found (%): | 81.29 | 6.85 | 5.57 |

EXAMPLE 25

N-(m-hydroxycinnamyl)-isoindoline

The process for the preparation of this compound and its physical properties will be given below. 4.8 grams of m-ethoxycarbonyloxycinnamyl chloride and 7.15 grams of isoindoline are dissolved in 70 milliliters of methanol, and the resulting solution is stirred for 2 hours at room temperature. After completion of the reaction, the methanol is distilled off, and the residue is extracted with benzene. The resulting extract is then purified by silica gel column chromatography and recrystallized from methanol to obtain 1.2 grams (yield 23.9%) of N-(m-hydroxycinnamyl)-isoindoline as crystals having a melting point of 164.5°–165.5° C.

Elementary analysis:

|  | C | H | N |
|---|---|---|---|
| Calcd. (%) for $C_{17}H_{17}NO$: | 81.24 | 6.82 | 5.57 |
| Found (%): | 81.28 | 6.81 | 5.59 |

EXAMPLE 26

N-(p-hydroxycinnamyl)-isoindoline

The process for preparing this compound will be given below along with its physical properties. A solution of 4.6 grams of p-acetoxycinnamyl chloride in 30 milliliters of ethanol is added dropwise to a solution of 6.49 grams of isoindoline in 20 milliliters of ethanol, and the resulting mixture is stirred overnight at room temperature. The precipitated crystals are collected by filtration and recrystallized from methanol to obtain 3.16 grams (yield 50%) of N-(p-hydroxycinnamyl)-isoindoline hydrochloride as crystals having a melting point of 213°–214° C. (decomposition).

Elementary analysis:

|  | C | H | N |
|---|---|---|---|
| Calcd. (%) for $C_{17}H_{17}NO \cdot HCl$: | 70.95 | 6.30 | 4.87 |
| Found (%): | 71.17 | 6.37 | 5.01 |

EXAMPLE 27

N-(3,4-dihydroxycinnamyl)-isoindoline

The process for preparing this compound and its physical properties will be given below. A solution of 2.6 grams of 3,4-diethoxycarbonyloxycinnamyl chloride in 10 milliliters of benzene is added dropwise with stirring to a solution of 3.8 grams of isoindoline in 20 milliliters of benzene while cooling the reaction system with ice. After completion of the dropping, the reaction is carried out for 2 hours at room temperature. On completion of the reaction, water and a large quantity of benzene are added followed by separating and collecting the benzene layer. After concentrating the benzene layer, it is left to stand under cooled conditions to precipitate crystals. When these crystals are recrystallized from a tetrahydrofuran-ether mixture, 1.1 grams (yield 52.1%) of N-(3,4-dihydroxycinnamyl)-isoindoline is obtained as crystals having a melting point of 60.5° C. (decomposition).

Elementary analysis:

|  | C | H | N |
|---|---|---|---|
| Calcd. (%) for $C_{17}H_{17}NO_2$: | 76.38 | 6.41 | 5.24 |
| Found (%): | 76.09 | 6.46 | 5.01 |

EXAMPLE 28

N-(4-hydroxy-3-methoxycinnamyl)-isoindoline

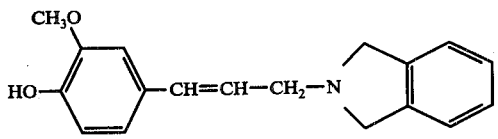

The process for preparing this compound will be described below, along with its physical properties. A solution of 5.6 grams of isoindoline in 50 milliliters of benzene is added dropwise to a solution of 4.7 grams of 4-ethoxycarbonyloxy-3-methoxy-cinnamyl chloride in 30 milliliters of benzene, after which the mixture is stirred for 1 hour at room temperature and then for 2 hours at 60° C. After completion of the reaction, water is added to the reaction mixture and extracted with benzene followed by distilling the solvent off to obtain an oily product, which is dissolved in a solution of 0.95 gram of potassium hydroxide in 50 milliliters of methanol and stirred for 30 minutes at room temperature. The reaction solution is then concentrated to dryness, and a 5% aqueous sodium hydroxide solution is added to the residue to precipitate crystals, which are filtered off. After adding an excess of ammonium chloride to the mother liquor, it is extracted with chloroform. The oily product obtained after distilling off the chloroform is transformed to a maleic acid salt by operating as in Example 15, which then is recrystallized from methanol to obtain 3.5 grams (yield 56.8%) of N-(4-hydroxy-3-methoxycinnamyl)-isoindoline.maleic acid salt as crystals having a melting point of 162°–164° C. (decomposition).

Elementary analysis:

|  | C | H | N |
|---|---|---|---|
| Calcd. (%) for $C_{19}H_{21}NO_2 \cdot C_4H_4O_4$: | 67.14 | 6.12 | 3.40 |
| Found (%): | 67.12 | 6.11 | 3.39 |

EXAMPLE 29

N(3-hydroxymethyl-4-hydroxy-cinnamyl)-isoindoline

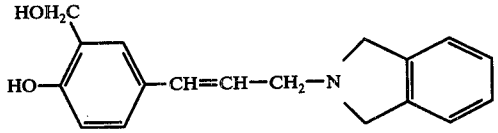

The process for preparing this compound and its physical properties will be given below. 0.53 gram of 3-isoindolino-1-[6-(2-phenyl-1,3-benzodioxanil)]-1-propene of the hereinafter-give Example 31 is dissolved in 40 milliliters of methanol followed by the addition of 11 milliliters of 0.2 N hydrochloric acid and stirring for 2.5 hours at 50° C. After distilling off the methanol and filtration of the residue, the filtrate is washed with benzene and rendered alkaline with sodium hydrogen-carbonate. The crystals that separate out are filtrably collected, water-washed and dried. The crystals are then recrystallized from methanol to obtain 0.24 gram (yield 59.5%) of N-(3-hydroxymethyl-4-hydroxy-cinnamyl)-isoindoline as yellow crystals having a melting point of 177°–178° C.

Elementary analysis:

|  | C | H | N |
|---|---|---|---|
| Calcd. (%) for $C_{18}H_{10}NO_2$: | 76.84 | 6.81 | 4.98 |
| Found (%): | 76.75 | 6.82 | 5.07 |

EXAMPLE 30

N-(3,4-methylenedioxycinnamyl)-isoindoline

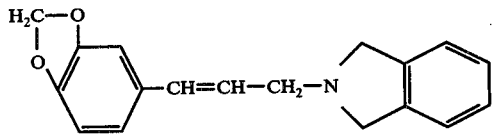

The process for the preparation of this compound and its physical properties will be given below. A solution of 5.8 grams of 3,4-methylenedioxycinnamyl bromide in 40 milliliters of benzene is added dropwise to a solution of 5.8 grams of isoindoline in 40 milliliters of benzene, following which the reaction mixture is stirred overnight at room temperature. After adding water to the reaction mixture, the benzene layer is separated and 20% hydrochloric acid is added thereto. The oily product that separates out is recrystallized from ethanol to obtain 1.1 gram (yield 14.5%) of N-(3,4-methylenedioxycinnamyl)-isoindoline hydrochloride as colorless crystals having a melting point of 209°–211° C. (decomposition).

Elementary analysis:

|  | C | H | N |
|---|---|---|---|
| Calcd. (%) for $C_{18}H_{17}No_2 \cdot HCl$: | 68.45 | 5.74 | 4.43 |

|          | C     | H    | N    |
|----------|-------|------|------|
| Found (%): | 68.02 | 5.75 | 4.42 |

EXAMPLE 31

3-Isoindolino-1-[6-(2-phenyl-1,3-benzodioxanil)]-1-propene

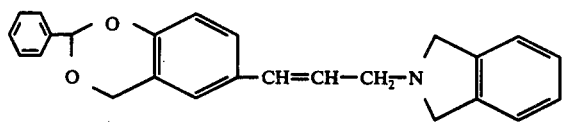

The process for preparing this compound and its physical properties will be given below. One gram of beta-[6-(2-phenyl-1,3-benzodioxanil)]-allyl alcohol is dissolved in 10 milliliters of benzene, after which 2 milliliters of benzene containing 0.32 gram of pyridine is added thereto. To the resulting solution is then added dropwise with stirring a solution of 0.476 gram of thionyl chloride in 12 milliliters of benzene while cooling the reaction system. After stirring the reaction mixture for 50 minutes, it is returned to room temperature, and the resulting yellow precipitate is filtered off. The milliliters of benzene containing 0.95 gram of isoindoline is then added to the filtrate with stirring at room temperature. After stirring the reaction mixture for 30 minutes, it is reacted for a further 5 hours at 50° C. After cooling the reaction mixture, it is filtered, following which the filtrate is distilled off, and the residue is submitted to silica gel column chromatography. When the benzene eluted portion is collected, 0.52 gram (yield 37.8%) of 3-isoindolino-1-[6-(2-phenyl-1,3-benzodioxanil)]-1-propene is obtained as yellow crystals. When this product is converted in a customary manner to a maleic acid salt, colorless acicular crystals having a melting point of 201°–202° C. are obtained.

Elementary analysis:

|                                          | C     | H    | N    |
|------------------------------------------|-------|------|------|
| Calcd. (%) for $C_{25}H_{23}NO_2 \cdot C_4H_4O_4$: | 71.74 | 5.61 | 2.89 |
| Found (%):                               | 71.96 | 5.63 | 2.77 |

EXAMPLE 32

Example 3 is repeated but using m-bromocinnamyl chloride instead of o-chlorocinnamyl chloride to obtain the compound No. 32 shown in the hereinbefore-given Table 1.

EXAMPLE 33

Example 17 is repeated but using 2,3-dimethoxycinnamyl chloride instead of p-methoxycinnamyl chloride to obtain the compound No. 33 shown in the hereinbefore-given Table 1.

We claim:
1. Isoindoline derivatives of the formula

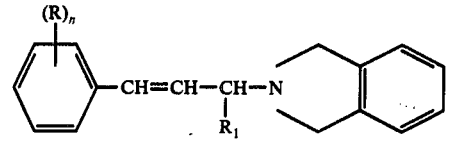

and the pharmaceutically acceptable acid addition salts thereof, wherein R represents a moiety selected from the group consisting of hydrogen, halogen, lower alkyl, lower alkoxy, nitro, hydroxy and hydroxy lower alkyl, and $n$ is a positive number from 1 to 3, which R's may be the same or different when $n$ is 2 or 3, and when $n$ is 2, the two R's may be joined to two vicinal carbon atoms in the phenyl ring to which the two R's are joined and may taken together form a lower alkylenedioxy group or the group

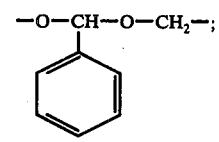

and $R_1$ is a member of the group consisting of hydrogen and lower alkyl.

2. Isoindoline derivatives and the pharmaceutically acceptable acid addition salts thereof of claim 1 wherein the lower alkyl represented by said R is a member of the group consisting of the straight chain and branched $C_1$–$C_4$ alkyl radicals, said lower alkoxy is a member of the group consisting of the $C_1$–$C_4$ alkoxy radicals, said hydroxy lower alkyl is a member of the group consisting of the hydroxy $C_1$–$C_4$ alkyl radicals, said lower alkylenedioxy is a member of the group consisting of the $C_1$–$C_2$ alkylenedioxy radicals, and said lower alkyl represented by $R_1$ is a member of the group consisting of the straight chain and branched $C_1$–$C_4$ alkyl radicals.

3. Isoindoline derivatives and the pharmaceutically acceptable acid addition salts thereof of claim 2 wherein said acid addition salt is an acid addition salt of an acid selected from the group consisting of hydrochloric acid, hydrobromic acid, hydroiodio acid, phosphoric acid, sulfuric acid, nitric acid, acetic acid, propionic acid, methanesulfonic acid, benzenesulfonic acid, oxalic acid, succinic acid, maleic acid, fumaric acid, citric acid, lactic acid, malic acid and tartaric acid.

4. The isoindoline derivatives and the pharmaceutically acceptable acid addition salts thereof of claim 2 wherein the lower alkyl represented by R is a member of the group consisting of straight chain and branched $C_1$–$C_3$ alkyl radicals.

5. The isoindoline derivatives and the pharmaceutically acceptable acid addition salts thereof of claim 2 wherein the hydroxy lower alkyl represented by R is a member of the group consisting of $C_1$–$C_3$ alkoxy radicals.

6. The isoindoline derivatives and the pharmaceutically acceptable acid addition salts thereof of claim 2 wherein R is a lower alkoxy radical selected from the group consisting of straight or branched hydroxy $C_1$–$C_3$ alkyl radicals.

7. The isoindoline derivatives and the pharmaceutically acceptable acid addition salts thereof of claim 2 wherein R is a hydroxy lower alkyl radical selected from the group consisting of hydroxy $C_1$–$C_2$ alkyl radicals.

8. The isoindoline derivatives and the pharmaceutically acceptable acid addition salts thereof of claim 2 wherein R is a lower alkylenedioxy selected from the group consisting of $C_1$–$C_2$ alkylenedioxy radicals.

* * * * *